US012632958B2

(12) United States Patent
Kim

(10) Patent No.: US 12,632,958 B2
(45) Date of Patent: May 19, 2026

(54) DEVICE AND METHOD FOR SUGGESTING OCCLUSAL PLANE

(71) Applicant: INDUSTRY-ACADEMIC COOPERATION FOUNDATION YONSEI UNIVERSITY, Seoul (KR)

(72) Inventor: Jong Eun Kim, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 370 days.

(21) Appl. No.: 18/266,214

(22) PCT Filed: Feb. 14, 2022

(86) PCT No.: PCT/KR2022/002159
§ 371 (c)(1),
(2) Date: Jun. 8, 2023

(87) PCT Pub. No.: WO2022/177243
PCT Pub. Date: Aug. 25, 2022

(65) Prior Publication Data
US 2024/0037735 A1 Feb. 1, 2024

(30) Foreign Application Priority Data
Feb. 16, 2021 (KR) ........................ 10-2021-0020639

(51) Int. Cl.
*G06T 7/00* (2017.01)
*G16H 10/60* (2018.01)
*G16H 30/40* (2018.01)
(52) U.S. Cl.
CPC ........... *G06T 7/0012* (2013.01); *G16H 10/60* (2018.01); *G16H 30/40* (2018.01);
(Continued)

(58) Field of Classification Search
None
See application file for complete search history.

(56) References Cited

U.S. PATENT DOCUMENTS

2012/0028211 A1* 2/2012 Palti ..................... A61C 9/0006
433/71
2018/0028294 A1* 2/2018 Azernikov ......... A61C 13/0004
(Continued)

FOREIGN PATENT DOCUMENTS

KR 10-2012-0027681 A 3/2012
KR 10-1952887 B1 6/2019
(Continued)

OTHER PUBLICATIONS

EPO Office Action, dated Dec. 4, 2024, for European Patent Application No. EP22756441 which corresponds to the above-identified U.S. application.
(Continued)

*Primary Examiner* — Samah A Beg
(74) *Attorney, Agent, or Firm* — LRK PATENT LAW FIRM

(57) ABSTRACT

An occlusal plane suggestion method according to an embodiment of the present invention comprises the steps in which: (a) an occlusal plane suggestion device receives at least one of first to fourth data for a person with normal occlusion and matches same to generate IVth image data; (b) the occlusal plane suggestion device analyzes the generated IVth image data to learn the relationship between a landmark, which is an anatomical singularity, and the occlusal plane of the person with normal occlusion; (c) the occlusal plane suggestion device receives at least one of first to fourth data about a patient; and (d) the occlusal plane suggestion device analyzes the received at least one of the first to fourth data about the patient on the basis of the learned relationship (Continued)

between the landmark and the normal occlusal plane to suggest and output an occlusal plane optimized for the patient.

12 Claims, 17 Drawing Sheets

(52) U.S. Cl.
CPC .............. *G06T 2207/10081* (2013.01); *G06T 2207/20081* (2013.01); *G06T 2207/30036* (2013.01)

(56) References Cited

U.S. PATENT DOCUMENTS

| | | | |
|---|---|---|---|
| 2019/0328489 A1 | 10/2019 | Capron-Richard et al. | |
| 2021/0192726 A1* | 6/2021 | Bergman | A61B 6/5217 |
| 2023/0390036 A1* | 12/2023 | Marshall | G06T 19/20 |
| 2024/0161292 A1* | 5/2024 | Bergman | G06T 7/0012 |
| 2025/0005772 A1* | 1/2025 | Ro | G06T 17/00 |

FOREIGN PATENT DOCUMENTS

| | | |
|---|---|---|
| KR | 10-2019-0137388 A | 12/2019 |
| KR | 10-2073478 B1 | 2/2020 |
| KR | 10-2020-0023703 A | 3/2020 |
| WO | 2020/048960 A1 | 3/2020 |

OTHER PUBLICATIONS

Search Report, mailed May 20, 2022, for International Application No. PCT/KR2022/002159.
Written Opinion, mailed May 20, 2022, for International Application No. PCT/KR2022/002159.

* cited by examiner

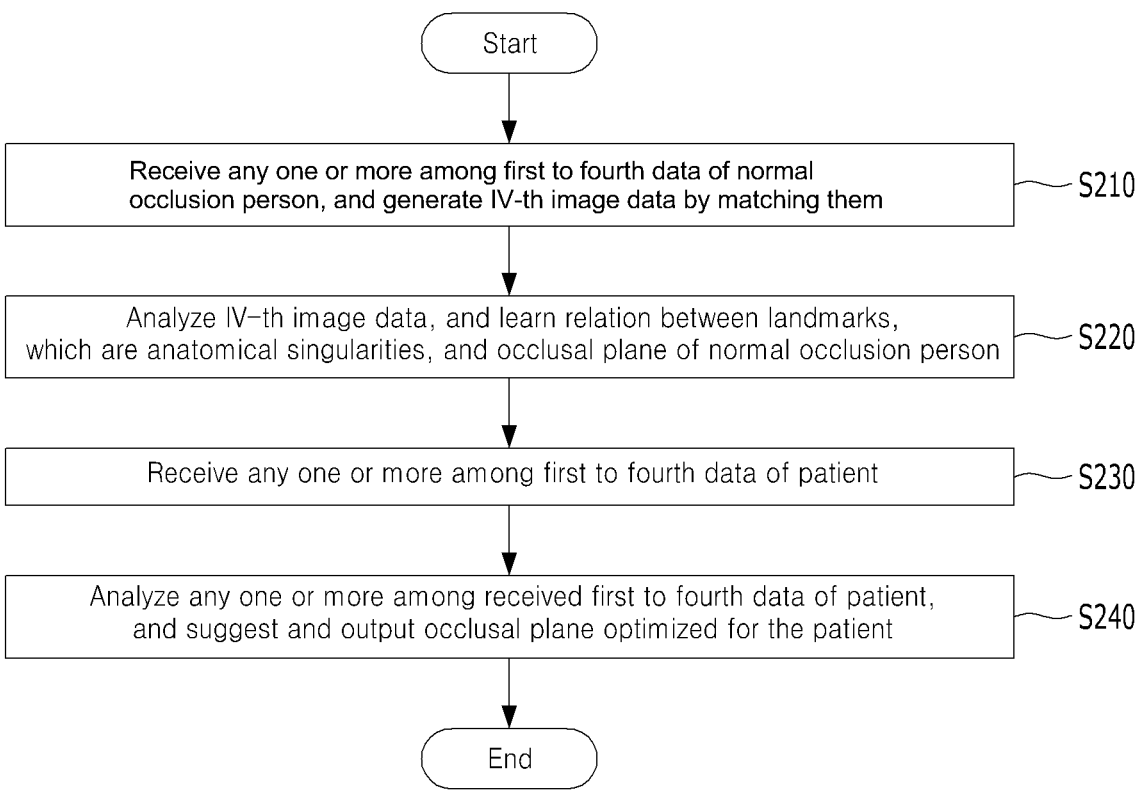

Start

Receive any one or more among first to fourth data of normal
occlusion person, and generate IV-th image data by matching them ——S210

Analyze IV-th image data, and learn relation between landmarks,
which are anatomical singularities, and occlusal plane of normal occlusion person ——S220

Receive any one or more among first to fourth data of patient ——S230

Analyze any one or more among received first to fourth data of patient,
and suggest and output occlusal plane optimized for the patient ——S240

End

FIG. 17
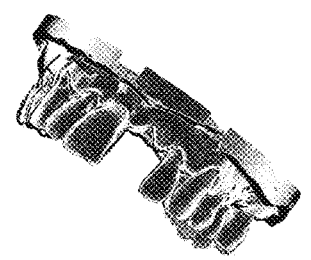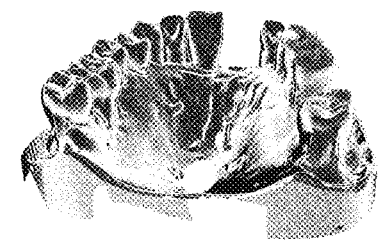

DEVICE AND METHOD FOR SUGGESTING OCCLUSAL PLANE

TECHNICAL FIELD

The present invention relates to a device and method for suggesting an occlusal plane, and more specifically, to a device and method for suggesting an occlusal plane, which can suggest an occlusal plane optimized for each patient based on learned data.

BACKGROUND ART

An occlusal plane means a front-to-back virtual plane formed by the occlusal surface of teeth as whole dentition, and it is general that a plane connecting the insulation of the mandibular central incisors and the buccal distal cusps of the mandibular second molars on both sides is considered as the occlusal plane. The occlusal plane may be used very preciously in making a treatment plan for a patient with collapsed occlusion, a patient with many missing teeth, a patient without remaining teeth, or the like, and it also may be used for treatment of teeth deviating from the occlusal plane in combination with space analysis of antagonist teeth, and therefore, it is treated as one of very important indicators in dental treatment.

Meanwhile, various methods have been adopted to suggest an occlusal plane optimized for a patient in the prior art, and representative methods thereof include a method of creating an occlusal plane with reference to major landmarks on the patient's face using a device called as face-bow, and transferring it to the articulator, a method of setting an occlusal plane by the clinician's own decision using an Ala-tragus Line that connects specific parts of nose and eyes, a method of using a degree of exposure of patient's teeth, and a method of performing a work of matching an occlusal plane on the surrounding landmarks using a Record Base and a Wax Rim made on the gingiva to replace the location of teeth in a way of trial-and-error using a device such as a Fox Plane or the like in the case of a patient with few teeth or a very large number of missing teeth.

Although any method is selected among the various conventional techniques, as a result of suggesting an occlusal plane may vary greatly according to the clinician's, i.e., operator's, level of skill, there is a problem in that it is difficult to expect treatment with a consistent quality from the viewpoint of a patient, and since face-bows or the like are very expensive equipment and difficult to maintain, there is also a problem in that the patient's burden for the suggestion of the occlusal plane using the face-bows and costs of treatment accompanied thereto increase.

Therefore, it is required to provide a new technique that can consistently suggest an occlusal plane optimized for a patient with an excellent quality regardless of the operator's level of skill and reduce the patient's burden for the suggestion of the occlusal plane and costs of treatment accompanied thereto at the same time. The present invention relates thereto.

DISCLOSURE OF INVENTION

Technical Problem

Therefore, the present invention has been made in view of the above problems, and it is an object of the present invention to provide a device and method for suggesting an occlusal plane, which can consistently suggest an occlusal plane optimized for a patient with an excellent quality regardless of the operator's level of skill.

Another object of the present invention is to provide a device and method for suggesting an occlusal plane, which can reduce the patient's burden for the suggestion of the occlusal plane and costs of treatment accompanied thereto.

The technical problems of the present invention are not limited to the technical problems mentioned above, and unmentioned other technical problems will be clearly understood by those skilled in the art from the following descriptions.

Technical Solution

To accomplish the above objects, according to one aspect of the present invention, there is provided an occlusal plane suggestion method comprising the steps of: (a) receiving any one or more among first to fourth data of a normal occlusion person, and generating an IV-th image data by matching the data, by an occlusal plane suggestion device; (b) analyzing the generated IV-th image data, and learning a relation between landmarks, which are anatomical singularities, and the occlusal plane of a normal occlusion person, by the occlusal plane suggestion device; (c) receiving any one or more among first to fourth data of a patient, by the occlusal plane suggestion device; and (d) analyzing any one or more among the received first to fourth data of the patient on the basis of the learned relation between the landmarks and the normal occlusal plane, and outputting a suggestion of an occlusion plane optimized for the patient, by the occlusal plane suggestion device.

According to an embodiment, any one among the first to fourth data of a normal occlusion person may be any one among oral cavity or oral model scan data of the normal occlusion person, face scan data with teeth exposed, Computed Tomography (CT) data, Cone Beam Computed Tomography (CBCT) data, and face scan data without teeth exposed.

According to an embodiment, any one or more among the cone beam computed tomography (CBCT) data and the face scan data without teeth exposed may be data marked with the landmarks.

According to an embodiment, step (a) may include the steps of: (a-1) generating I-th image data by matching oral cavity or oral model scan data, which is a first data of a normal occlusion person, and face scan data with teeth exposed, which is a second data; (a-2) generating II-th image data by matching oral or oral model scan data, which is a first data of a normal occlusion person, and CBCT data, which is a third data; (a-3) generating III-th image data by matching face scan data with teeth exposed, which is a second data of a normal occlusion person, and face scan data without teeth exposed, which is a fourth data; and (a-4) generating IV-th image data by matching the I-th image data, the II-th image data, and the III-th image data.

According to an embodiment, the occlusal plane suggestion method may further comprise, after step (a-4), the step of (a-5) removing the face scan data with teeth exposed, which is a second data, from the IV-th image data.

According to an embodiment, the I-th image data may be generated by matching the oral cavity or oral model scan data, which is a first data of a normal occlusion person, and the face scan data with teeth exposed, which is a second data, on the basis of teeth of an anterior exposed area.

According to an embodiment, the II-th image data may be generated by matching the oral cavity or oral model scan data, which is a first data, and the CBCT data, which is a third data, on the basis of entire teeth.

According to an embodiment, the first data of the patient may be oral cavity or oral model scan data of the patient.

According to an embodiment, the landmarks may be any one or more among nasion, glabella, exocanthion right, exocanthion left, endocanthion right, endocanthion left, pronasale, subnasale, alar right, alar left, crista philtri right, crista philtri left, labiale superious, chellion right, chellion left, stomion, labiale inferious, sublabiale, pogonion, gnathion, menton, tragus right, tragus left, gonion right, gonion left, tragion, basion, anterior nasal spine, posterior nasal spine, point a (point of maximum midline concavity on the maxilla), point b (point of maximum midline concavity on the mandibular symphysis), pogonion, menton, gnathion, left porion, right porion, left orbitale, right orbitale, left condylion, right condylion, left gonion, right gonion, left zygion, and right zygion.

According to an embodiment, the learning at step (b) may be a learning using any one or more among a generative adversarial network (GAN) and a volume-to-volume regression.

According to an embodiment, step (d) may include the steps of: (d-1) marking and outputting teeth deviating from the suggested occlusal plane optimized for the patient; and (d-2) outputting a part or a volume of the teeth deviating from the suggested occlusal plane optimized for the patient.

According to an embodiment, the part or volume of the teeth of the patient deviating from the suggested occlusal plane optimized for the patient may be output in response to a selected threshold value.

According to another aspect of the present invention, there is provided an occlusal plane suggestion device comprising: one or more processors; a network interface; a memory for loading a computer program executed by the processor; and a storage for storing large-capacity network data and the computer program, wherein the computer program executes, by the one or more processors, (A) an operation of receiving any one or more among first to fourth data of a normal occlusion person, and generating an IV-th image data by matching the data; (B) an operation of analyzing the generated IV-th image data, and learning a relation between landmarks, which are anatomical singularities, and the occlusal plane of a normal occlusion person; (C) an operation of receiving any one or more among first to fourth data of a patient; and (D) an operation of analyzing any one or more among the received first to fourth data of the patient on the basis of the learned relation between the landmarks and the occlusal plane of a normal occlusion person, and outputting a suggestion of an occlusion plane optimized for the patient.

According to another aspect of the present invention, there is provided a computer program stored in a medium to execute, in combination with a computing device, the steps of: (AA) receiving any one or more among first to fourth data of a normal occlusion person, and generating an IV-th image data by matching the data; (BB) analyzing the generated IV-th image data, and learning a relation between landmarks, which are anatomical singularities, and the occlusal plane of a normal occlusion person; (CC) receiving any one or more among first to fourth data of a patient; and (DD) analyzing any one or more among the received first to fourth data of the patient on the basis of the learned relation between the landmarks and the occlusal plane of a normal occlusion person, and outputting a suggestion of an occlusion plane optimized for the patient.

Advantageous Effects

According to the present invention as described above, as an occlusal plane optimized for a patient is suggested by simply inputting any one or more among first to fourth data of the patient into an occlusal plane suggestion device, there is an effect of suggesting an occlusal plane optimized for the patient with a consistent quality regardless of the operator's level of skill.

In addition, since equipment that is expensive and difficult to maintain such as a face-bow or the like is not required, and it is sufficient to pay only an initial purchase cost for the occlusal plane suggestion device or a predetermined fee for using the device when it is implemented as a server, there is an effect of reducing the patient's burden for the suggestion of an occlusal plane and costs of treatment accompanied thereto.

In addition, since an operator may separately prepare and proceed various treatment plans by adjusting a threshold value when an occlusal plane optimized for a patient is suggested, there is an effect of guaranteeing a degree of freedom in establishing a treatment plan.

The effects of the present invention are not limited to the effects mentioned above, and unmentioned other effects will be clearly understood by those skilled in the art from the following descriptions.

BRIEF DESCRIPTION OF THE DRAWINGS

FIG. 2 is a flowchart illustrating representative steps of an occlusal plane suggestion method according to a second embodiment of the present invention.

FIG. 17 is a view exemplarily showing a view of observing from various angles by rotating the occlusal plane optimized for the patient and a part of teeth deviating from the occlusal plane shown in FIG. 16.

BEST MODE FOR CARRYING OUT THE INVENTION

Hereinafter, preferred embodiments of the present invention will be described in detail with reference to the accompanying drawings. Advantages and features of the present invention and methods for achieving them will become clear with reference to the embodiments described below in detail in conjunction with the accompanying drawings. However, the present invention is not limited to the embodiments disclosed below and may be implemented in various different forms, and these embodiments are provided only to make the disclosure of the present invention complete and to fully inform those skilled in the art of the scope of the present invention, and the present invention is only defined by the scope of the claims. Like reference numbers refer to like elements throughout the specification.

Unless otherwise defined, all terms (including technical and scientific terms) used in this specification can be used as a meaning that can be commonly understood by those skilled in the art. In addition, terms defined in commonly used dictionaries are not interpreted ideally or excessively unless explicitly and specifically defined. Terms used in this specification are for describing the embodiments and are not intended to limit the present invention. In this specification, singular forms also include plural forms unless specifically stated otherwise in a phrase.

"Comprises" and/or "comprising" used in the specification means that a mentioned component, step, operation, and/or element does not preclude the presence or addition of one or more other components, steps, operations, and/or elements.

Figure 1:
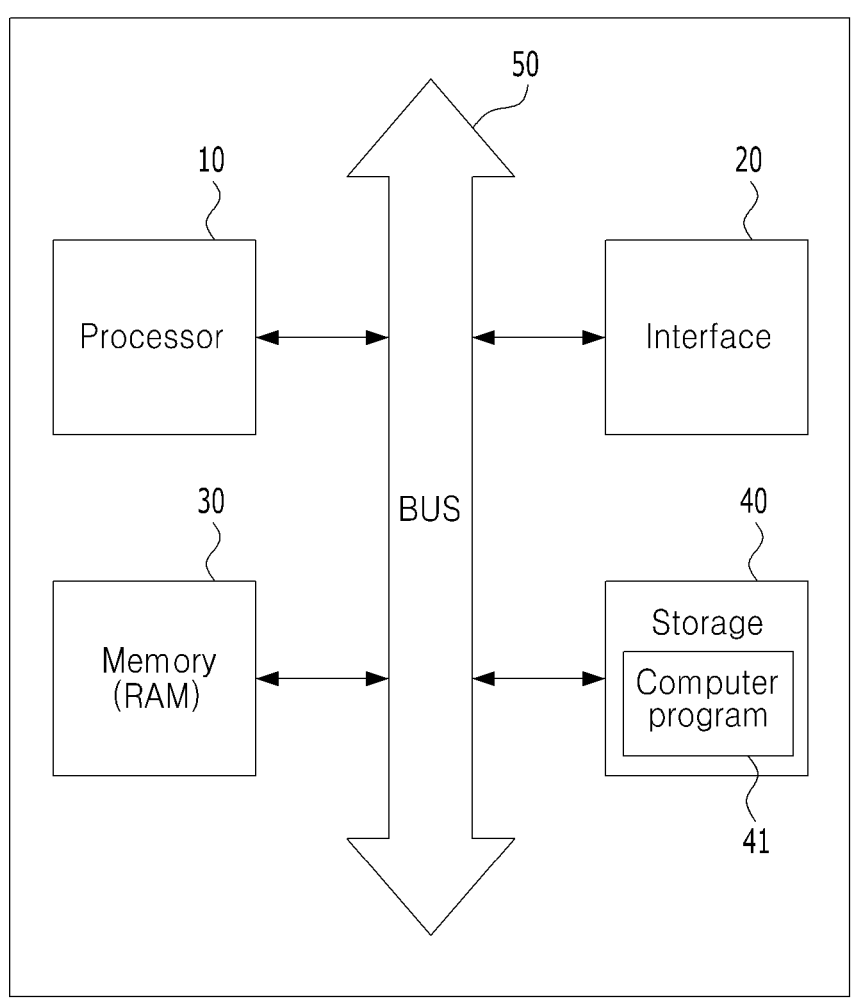
FIG. 1 is a view showing the overall configuration of an occlusal plane suggestion device according to a first embodiment of the present invention.

FIG. 1 is a view showing the overall configuration of an occlusal plane suggestion device according to a first embodiment of the present invention.

However, this is only a preferred embodiment for achieving the objects of the present invention, and some components may be added or deleted as needed, and other components may also perform the functions performed by any one component.

An occlusal plane suggestion device 100 according to a first embodiment of the present invention may include a processor 10, a network interface 20, a memory 30, a storage 40, and a data bus 50 connecting them.

The processor 10 controls the overall operation of each component. The processor 10 may be any one among a central processing unit (CPU), a microprocessor unit (MPU), a microcontroller unit (MCU), and a type of processor widely known in the art. In addition, the processor 10 may perform operations of at least one application or program to perform the occlusal plane suggestion method according to a second embodiment of the present invention.

The network interface 20 supports wired and wireless Internet communication of the occlusal plane suggestion device 100 according to a first embodiment of the present invention, and may support other known communication methods. Accordingly, the network interface 20 may be configured to include a communication module according thereto.

The memory 30 may store various types of data, commands and/or information, and load one or more computer programs 41 from the storage 40 to perform the occlusal plane suggestion method according to a second embodiment of the present invention. Although RAM is shown as a kind of the memory 30 in FIG. 1, it goes without saying that various types of storage media can be used as the memory 30.

The storage 40 may non-temporarily store one or more computer programs 41 and large-scale network data 42. The storage 40 may be any one among a non-volatile memory such as read only memory (ROM), erasable programmable ROM (EPROM), electrically erasable programmable ROM (EEPROM), flash memory, or the like, a hard disk, a detachable disk, and any type of computer-readable recording medium widely known in the art.

The computer program 41 may be loaded on the memory 30 and execute, by one or more processors 10, (A) an operation of receiving any one or more among first to fourth data of a normal occlusion person, and generating an IV-th image data by matching the data; (B) an operation of analyzing the generated IV-th image data, and learning the relation between landmarks, which are anatomical singularities, and the occlusal plane of a normal occlusion person; (C) an operation of receiving any one or more among first to fourth data of a patient; and (D) an operation of analyzing any one or more among the received first to fourth data of the patient on the basis of the learned relation between the landmarks and the occlusal plane of a normal occlusion person, and outputting a suggestion of an occlusion plane optimized for the patient.

The operations performed by the computer program 41 briefly mentioned so far may be regarded as a function of the computer program 41, and a more detailed description will be provided below in the description of the occlusal plane suggestion method according to a second embodiment of the present invention.

The data bus 50 functions as a passage of commands and/or information between the processor 10, the network interface 20, the memory 30, and the storage 40 described above.

The occlusal plane suggestion device 100 according to a first embodiment of the present invention described above may be an independent electronic or mechanical device, or may be a tangible physical server or an intangible cloud server. In this case, the computer program 41 will be a key component that executes the operations mentioned above, and known dental treatments or treatment programs may also be installed in the server, and the operations mentioned above may be implemented as a function of the known dental treatments or treatment programs.

In addition, although it is not separately described or shown in the drawings, the occlusal plane suggestion device 100 according to a first embodiment of the present invention may have a display unit (not shown) included therein or may be connected to an external display device (not shown) to output image data.

Hereinafter, the occlusal plane suggestion method according to a second embodiment of the present invention will be described with reference to FIGS. 2 to 17.

FIG. 2 is a flowchart illustrating representative steps of an occlusal plane suggestion method according to a second embodiment of the present invention.

This is only a preferred embodiment in achieving the objects of the present invention, and some steps may be added or deleted as needed, and furthermore, any one step may be included in another step.

Meanwhile, it is assumed that all the steps are performed by the occlusal plane suggestion device 100 according to a first embodiment of the present invention.

First of all, the occlusal plane suggestion device 100 receives any one or more among first to fourth data of a normal occlusion person, and generates the IV-th image data by matching the data (S210).

Here, any one among the first to fourth data of a normal occlusion person may be any one among oral cavity or oral model scan data of the normal occlusion person, face scan data with teeth exposed, Computed Tomography (CT) data, Cone Beam Computed Tomography (CBCT) data, and face scan data without teeth exposed (since handling of the CT data and the CBCT data is not significantly different, it will be described below on the basis of the CBCT data). Among these data, any one or more among the CBCT data and the face scan data without teeth exposed may be data marked with landmarks, which are anatomical singularities, and in order to improve accuracy of learning performed at step S220 described below, it is preferable to receive all of the first to fourth data rather than any one data.

Figure 3:
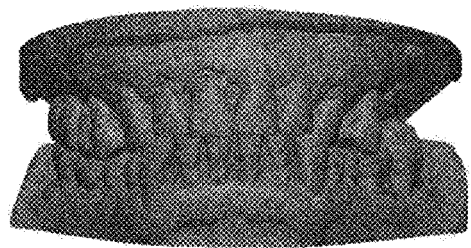
FIG. 3 is a view exemplarily showing oral cavity or oral model scan data of a normal occlusion person.
Figure 4:
FIG. 4 is a view exemplarily showing face scan data with teeth exposed.
Figure 5:
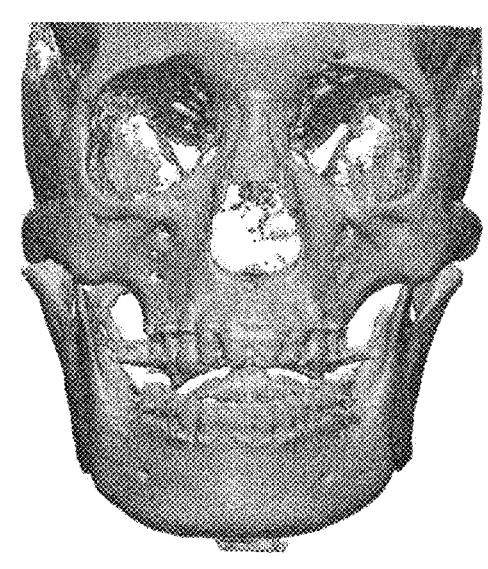
FIG. 5 is a view exemplarily showing CBCT data.
Figure 6:
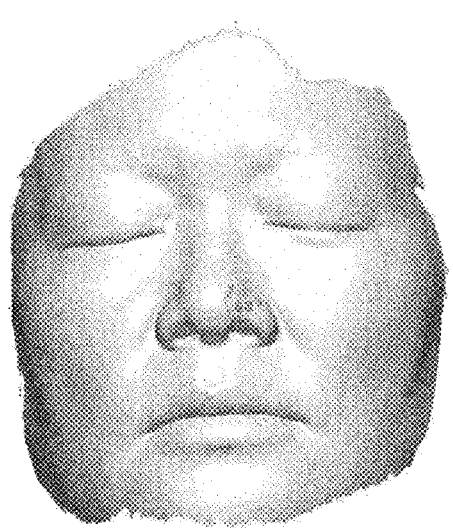
FIG. 6 is a view exemplarily showing face scan data without teeth exposed.

Meanwhile, FIG. 3 shows oral cavity or oral model scan data of a normal occlusion person, FIG. 4 shows face scan data with teeth exposed, FIG. 5 shows CBCT data, and FIG. 6 shows face scan data without teeth exposed as an example, and it can be confirmed that all of these are one of three-dimensional image data. Accordingly, when any one or more among the first to fourth data are received from a device that photographs or generates the corresponding image data, and it is an image data photographed or generated by one component of the occlusal plane suggestion device 100 according to a first embodiment of the present invention, this is the broadest concept sense including a case where the processor 10 receives the data from a corresponding component, and the like.

IV-th image data, which is an output of step S210, is generated by matching any one or more among the first to fourth data, and this will be described below with reference to FIG. 7.

Figure 7:
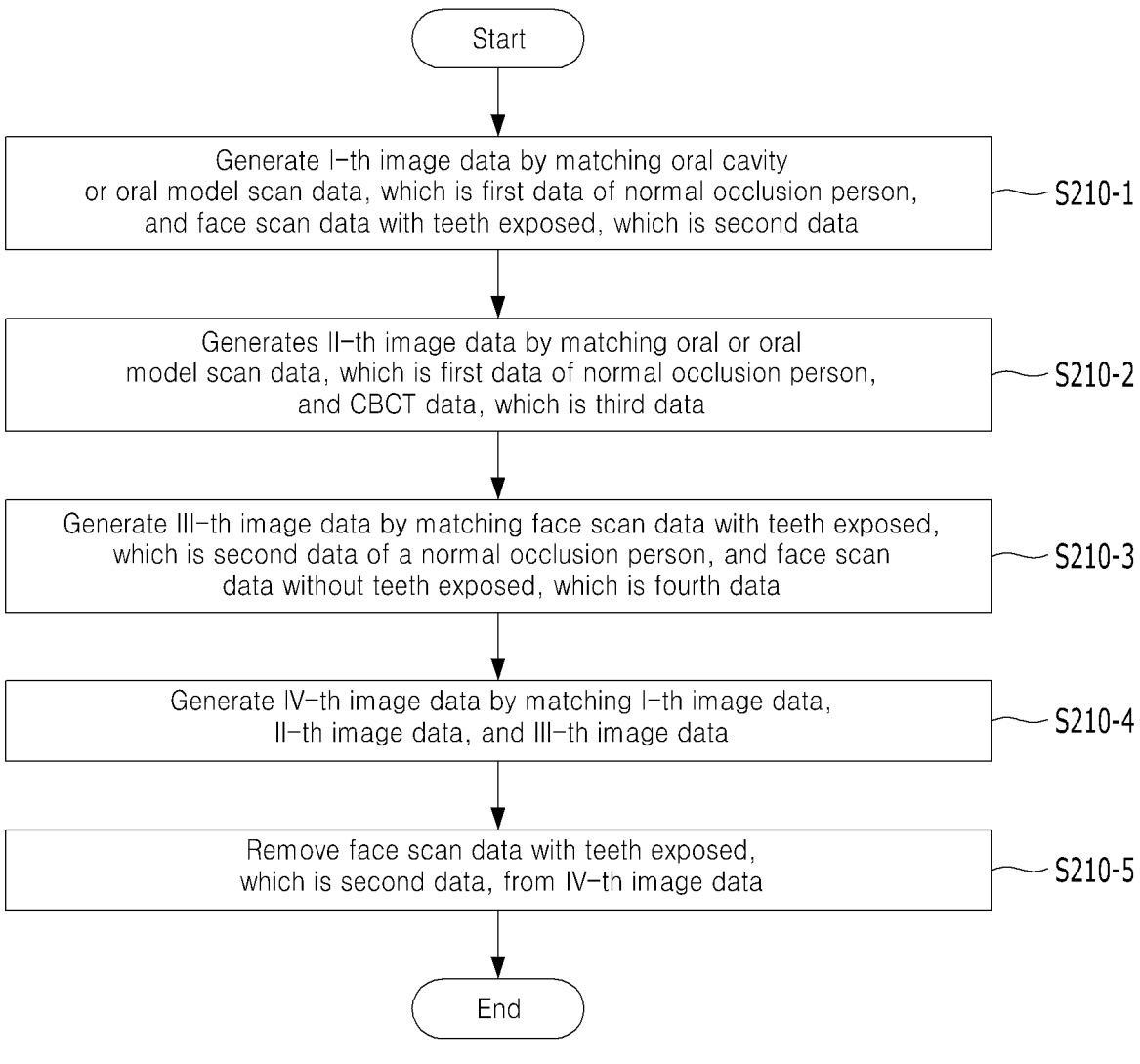
FIG. 7 is a flowchart illustrating the step of generating IV-th image data in an occlusal plane suggestion method according to a second embodiment of the present invention.

FIG. 7 is a flowchart illustrating the step of generating IV-th image data in an occlusal plane suggestion method according to a second embodiment of the present invention.

This is only a preferred embodiment in achieving the objects of the present invention, and some steps may be added or deleted as needed, and furthermore, any one step may be included in another step.

First, the occlusal plane suggestion device 100 generates I-th image data by matching oral cavity or oral model scan data, which is a first data of a normal occlusion person, and face scan data with teeth exposed, which is a second data (S210-1).

Figure 8:
FIG. 8 is a view exemplarily showing I-th image data.

As the I-th image data generated by matching the oral cavity or oral model scan data, which is a first data of a normal occlusion person shown in FIG. 3, and the face scan data with teeth exposed, which is a second data shown in FIG. 4, is shown in FIG. 8 as an example, it can be confirmed that the I-th image data generated by matching the oral cavity or oral model scan data, which is a first data of a normal occlusion person, and the face scan data with teeth exposed, which is a second data, is generated by matching on the basis of the teeth of the anterior exposed area.

In addition to generation of the I-th image data, the occlusal plane suggestion device 100 generates II-th image data by matching oral or oral model scan data, which is a first data of a normal occlusion person, and CBCT data, which is a third data (S210-2).

As the II-th image data generated by matching the oral cavity or oral model scan data, which is a first data of a normal occlusion person shown in FIG. 3, and the CBCT data, which is a third data shown in FIG. 5, is shown in FIG.

9 as an example, it may be said that matching the II-th image data is generating the image data by matching on the basis of the entire teeth, rather than the teeth of the anterior exposed area, unlike the I-th image data described above.

In addition to generation of the I-th image data and the II-th image data, the occlusal plane suggestion device 100 generates III-th image data by matching face scan data with teeth exposed, which is a second data of a normal occlusion person, and face scan data without teeth exposed, which is a fourth data (S210-3).

Figure 10:
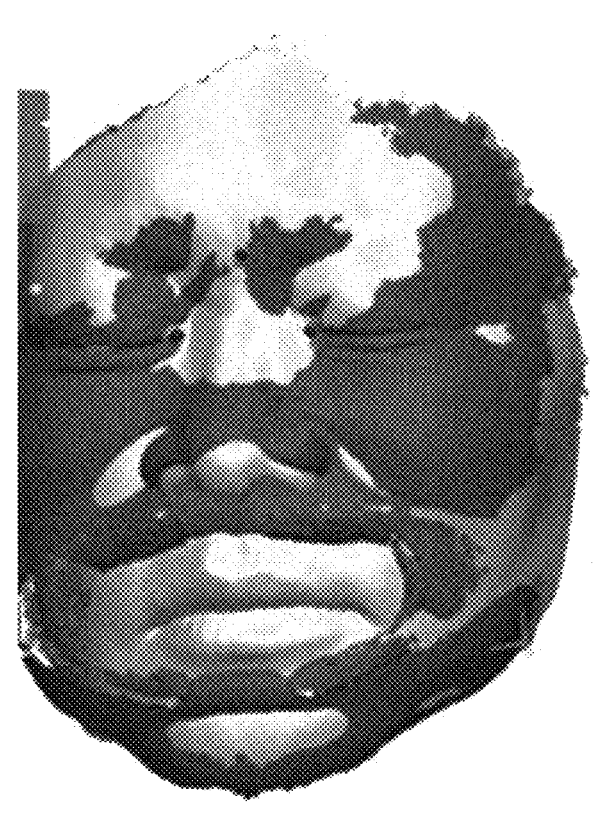
FIG. 10 is a view exemplarily showing III-th image data.

As the III-th image data generated by matching the face scan data with teeth exposed, which is a second data shown in FIG. 4, and the face scan data without teeth exposed, which is a fourth data shown in FIG. 6, is shown in FIG. 10 as an example, it may be said that matching the III-th image data is generating the image data by matching on the basis of any one or more of the landmarks, which are anatomical singularities, unlike the I-th image data and the II-th image data described above.

When all the I-th image data, II-th image data, and III-th image data are generated, the occlusal plane suggestion device 100 generates IV-th image data by matching these image data (S210-4).

As described above, since the I-th image data is generated by matching oral cavity or oral model scan data, which is a first data of a normal occlusion person, and face scan data with teeth exposed, which is a second data, the II-th image data is generated by matching oral cavity or oral model scan data, which is a first data of a normal occlusion person, and CBCT data, which is a second data, and the III-th image data is generated by matching face scan data with teeth exposed, which is a second data of a normal occlusion person, and face scan data without teeth exposed, which is a fourth data, the IV-th image data (first data+second data+third data+fourth data) may be generated by matching the I-th image data (first data+second data) and the II-th image data (first data+third data) on the basis of the oral cavity or oral model scan data, which is a first data of a normal occlusion person (first data+second data+third data), and matching the III-th image data (second data+fourth data) on the basis of the face scan data with teeth exposed, which is a second data, and therefore, and the order of matching the I-th image data, II-th image data, and III-th image data is irrelevant. For example, as the I-th image data (first data+second data) and the III-th image data (second data+fourth data) are matched (first data+second data+fourth data) on the basis of the face scan data with teeth exposed, which is a second data, and the II-th image data (first data+third data) is matched on the basis of the oral cavity or oral model scan data, which is a first data, the IV-th image data (first data+second data+third data+fourth data) may be generated.

Figure 9:
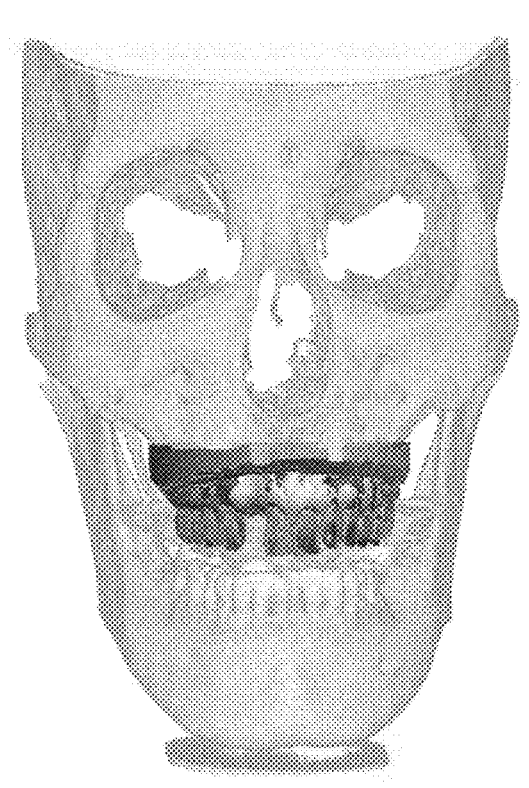
FIG. 9 is a view exemplarily showing II-th image data.
Figure 11:
FIG. 11 is a view exemplarily showing IV-th image data.
Figure 12:
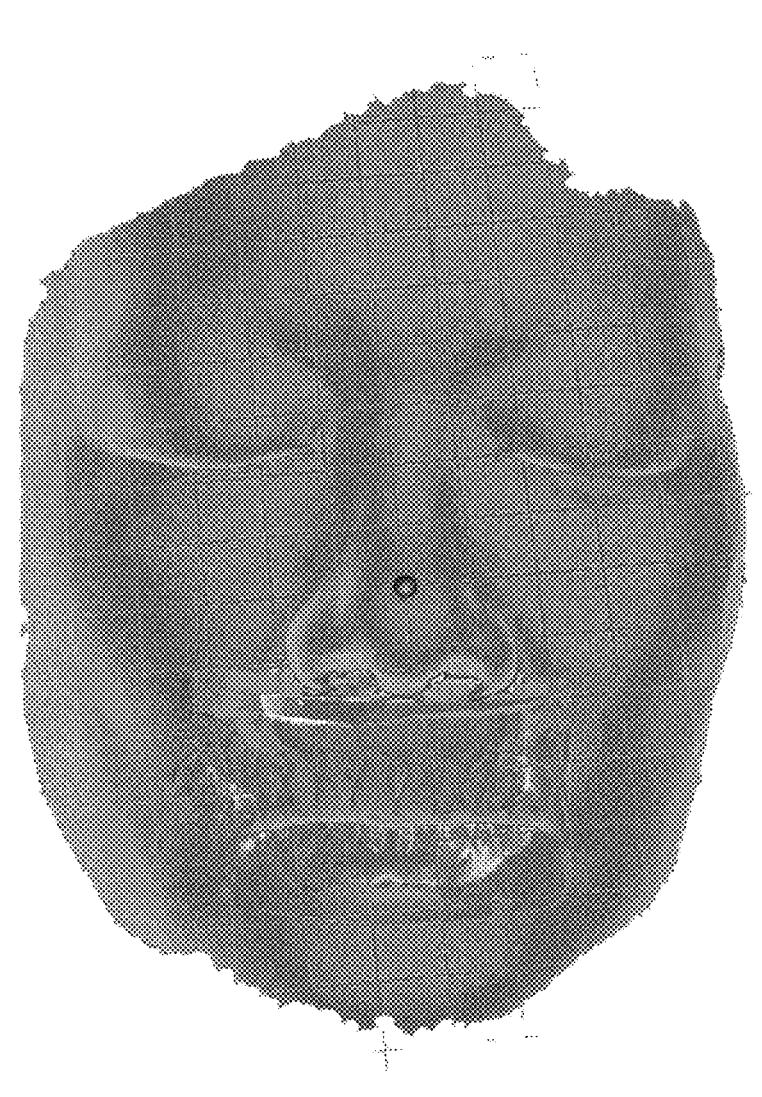
FIG. 12 is a view exemplarily showing image data obtained by deleting a second data from IV-th image data shown in FIG. 11.

The IV-th image data generated by matching the I-th image data shown in FIG. 8, the II-th image data shown in FIG. 9, and the III-th image data shown in FIG. 10 is shown in FIG. 11 as an example, and the second data, which is face scan data with teeth exposed, is very important in the matching the image data, since it is data with teeth exposed, which is a clear criterion for the matching, compared to other indexes.

Meanwhile, when the IV-th image data is generated, the occlusal plane suggestion device 100 removes the face scan data with teeth exposed, which is a second data, from the IV-th image data (S210-5), since although the second data is data with teeth exposed, which is a clear criterion for matching, the patient's face is inevitably frowned or distorted in the process of exposing the teeth. This can be confirmed by comparing the face scan data with teeth exposed, which is a second data shown in FIG. 4, with the face scan data without teeth exposed, which is a fourth data shown in FIG. 6, and compared to FIG. 6 in which the patient does not expose teeth and has a calm expression, it can be confirmed, in the case of FIG. 4, that the eyebrows are frowned and wrinkles are formed around the eyes and mouth by exposing the teeth. For this reason, the face scan data with teeth exposed, which is a second data, is used only in the process of matching and removed thereafter, and FIG. 12 exemplarily shows image data obtained by deleting the second data from the IV-th image data shown in FIG. 11.

Now, go back to the description of FIG. 2 again.

When the IV-th image data is generated, the occlusal plane suggestion device 100 analyzes the IV-th image data and learns the relation between the landmarks, which are anatomical singularities, and the occlusal plane of a normal occlusion person (S220).

Figure 13:
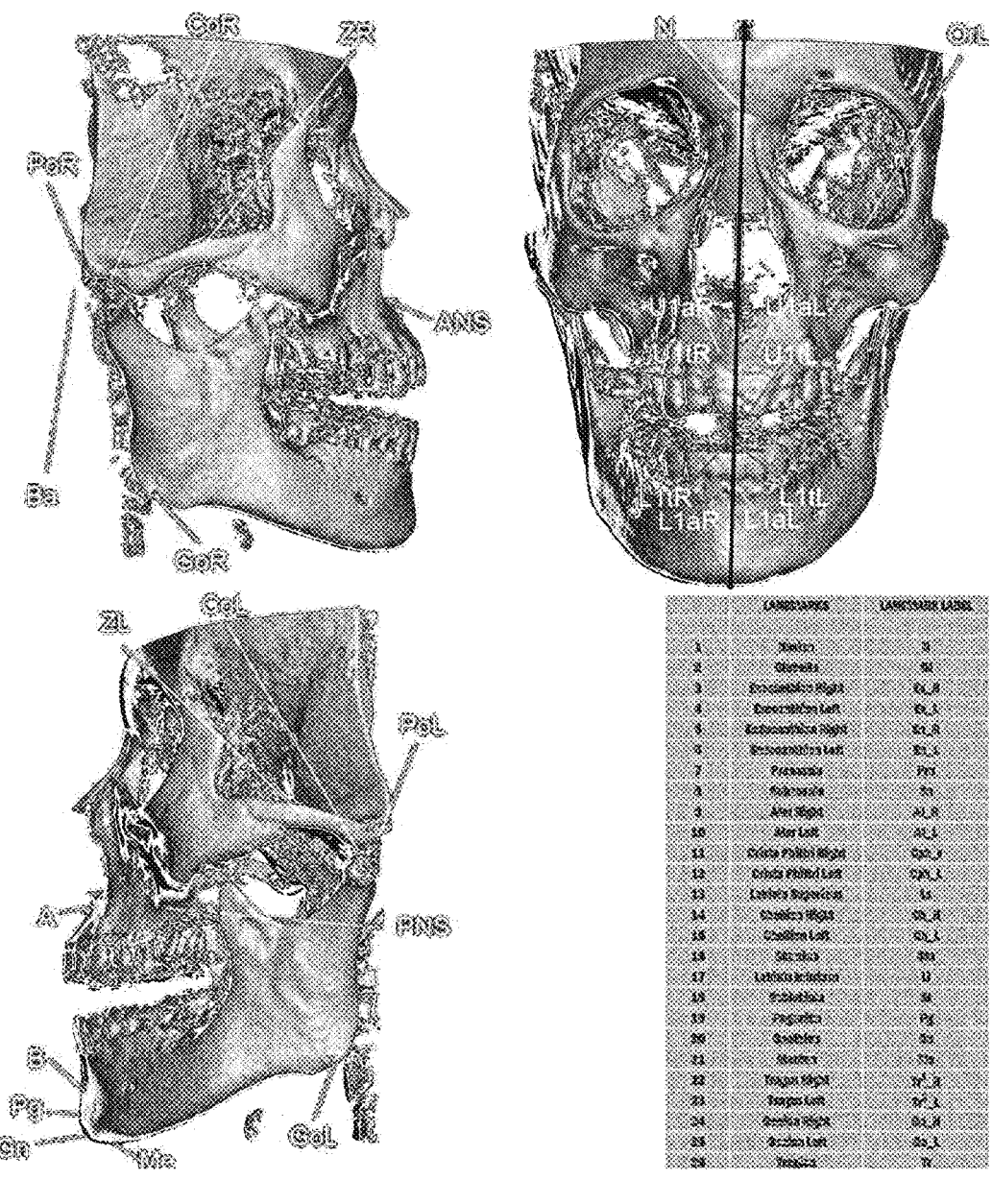
FIG. 13 is a view exemplarily showing landmarks that are anatomical singularities.

Here, as the landmarks, which are anatomical singularities, representative landmarks are shown in FIG. 13 as an example, and more specifically, they may be any one or more among nasion, glabella, exocanthion right, exocanthion left, endocanthion right, endocanthion left, pronasale, subnasale, alar right, alar left, crista philtri right, crista philtri left, labiale superious, chellion right, chellion left, stomion, labiale inferious, sublabiale, pogonion, gnathion, menton, tragus right, tragus left, gonion right, gonion left, tragion, basion, anterior nasal spine, posterior nasal spine, point a (point of maximum midline concavity on the maxilla), point b (point of maximum midline concavity on the mandibular symphysis), pogonion, menton, gnathion, left porion, right porion, left orbitale, right orbitale, left condylion, right condylion, left gonion, right gonion, left zygion, and right zygion, and in addition, any known landmark used in the dental treatment may be possible, and may be a landmark marked in any one or more among the CBCT data, i.e., third data, and the face scan data with teeth not exposed, i.e., fourth data.

Meanwhile, an occlusal plane of a normal occlusion person needs to be produced before learning the relation between landmarks, which are anatomical singularities, and the occlusal plane of a normal occlusion person, and therefore, the occlusal plane suggestion device 100 may perform the step of producing an occlusal plane of a normal occlusion person on the IV-th image data between steps S210 and S220 (S215).

Figure 14:
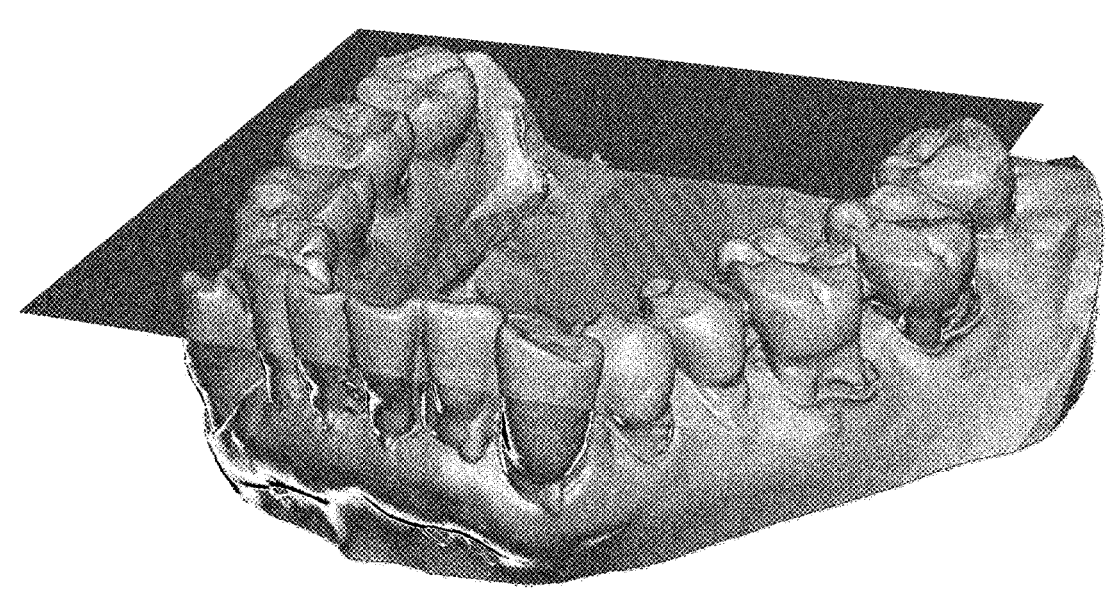
FIG. 14 is a view exemplarily showing an occlusal plane produced from a first data.

The oral cavity or oral model scan data, which is a first data, of a normal occlusion person may be used in producing an occlusal plane of the normal occlusion person, and since it is easy to confirm the incisal tip and the cusp tip of the teeth, the occlusal plane suggestion device 100 may produce an occlusal plane having a slightly curved shape on the basis of the incisal tip and the cusp tip, and this is shown in FIG. 14 as an example.

Meanwhile, the step of producing an occlusal plane of a normal occlusion person using oral cavity or oral model scan data of a normal occlusion person, which is a first data, does not have to be performed between steps S210 and S220, and the producing step may be performed immediately after receiving the oral cavity or oral model scan data of a normal occlusion person, which is a first data, at step S210, or an oral cavity or oral model scan data of a normal occlusion person, which is a first data, of a state in which an occlusal plane of a normal occlusion person is previously produced may be received, and it may be performed at any one step of steps S210-1 to S210-5 of generating image data or between any one step and another step.

The relation between the landmarks and the occlusal plane learned by the occlusal plane suggestion device 100 may be the shortest distance, the longest distance, and an average distance from each landmark to the occlusal plane, an angle between a straight-line vector connecting two or more landmarks among a plurality of landmarks and the occlusal plane, an angle between a plane connecting two or more landmarks among a plurality of landmarks and the occlusal plane, or a type of landmark included in an arbitrary plane having the highest degree of parallelism with the occlusal plane, and the distance, the angle, and the like between the two planes. In addition, whatever that can express the relation between a specific landmark and the occlusal plane, a straight-line vector connecting two or more landmarks among a plurality of landmarks and the occlusal plane, or a plane connecting two or more landmarks among a plurality of landmarks and the occlusal plane may be learned as the relation between a landmark and the occlusal plane.

Meanwhile, since learning of the relation between the landmarks and the occlusal plane described above may use a deep learning technique, more specifically, a generative adversarial network (GAN) technique, this may be performed by the processor 10 included in the occlusal plane suggestion device 100 according to a first embodiment of the present invention, and it is possible to proceed the learning using a known deep learning algorithm, such as a volume to volume regression or the like, as well as a generative adversarial network.

Once the relation between the landmarks and the occlusal planes of a normal occlusion person has been learned, the occlusal plane suggestion device 100 receives any one or more among the first to fourth data of a patient (S230).

Here, the patient means a person who needs to be provided with a dental treatment plan through an analysis of the relation between the patient's current dental condition and an occlusal plane optimized for the patient, such as a patient with collapsed occlusion, a patient with many missing teeth, or a patient without remaining teeth.

Meanwhile, the data that the occlusal plane suggestion device 100 receives is any one or more among the first to fourth data of the patient, and it is most preferable to receive all of the first data of the patient's oral cavity or oral model scan data, the second data of the patient's face scan data with teeth exposed, the third data of the patient's CBCT data, and the fourth data of the patient's face scan data without teeth exposed, since accuracy of the output of the result according to the input will be the highest as the type of the data is the same as that of the learning about the normal occlusion person. In this case, since the first to fourth data of the patient also go through the same matching steps as steps S210-1 to S210-5 like the first to fourth data of the normal occlusion person, detailed description will be omitted to prevent redundant description.

In addition, in some cases, the data that the occlusal plane suggestion device 100 receives may be the first data of the patient's oral cavity or oral model scan data and the third data of the patient's CBCT data, or the first data of the patient's oral cavity or oral model scan data, the second data of the patient's face scan data with teeth exposed, and the fourth data of the patient's face scan data without teeth exposed, since it does not make a problem in receiving a suggestion of an occlusal plane optimized for the patient at step S240 described below since landmarks are marked in specific data in both the former and latter cases.

However, apart from receiving a suggestion of an occlusal plane optimized for the patient, there may be a difference in accuracy, and since the number of landmarks marked in the third data of the patient's CBCT data is greater than the number of landmarks marked in the fourth data of the patient's face scan data without teeth exposed, when the accuracy should be considered, the accuracy can be improved in the order of the first, second and fourth data, the first and third data, and the first to fourth data of the patient.

When the first data of the patient is received, an occlusal plane optimized for the patient is suggested and output by analyzing any one or more among the received first to fourth data of the patient on the basis of the relation between the landmarks learned by the occlusal plane suggestion device 100 and the occlusal plane of the normal occlusion person (S240).

Since the relation between the landmarks, which are anatomical singularities, and the occlusal plane of a normal occlusion person, more specifically, all relations whatever that can express the relation between a specific landmark and the occlusal plane, a straight-line vector connecting two or more landmarks among a plurality of landmarks and the occlusal plane, or a plane connecting two or more landmarks among a plurality of landmarks and the occlusal plane have been learned at step S220, in addition to the shortest distance, the longest distance, and an average distance from each landmark to the occlusal plane, an angle between a straight-line vector connecting two or more landmarks among a plurality of landmarks and the occlusal plane, an angle between a plane connecting two or more landmarks among a plurality of landmarks and the occlusal plane, and a type of landmark included in an arbitrary plane having the highest degree of parallelism with the occlusal plane, and the distance, the angle, and the like between the two planes, when only any one or more among the first to fourth data of the patient are received, an occlusal plane optimized for the patient can be suggested by putting the relation between the landmark included therein and the current teeth of the patient into the learning result.

On the other hand, in outputting the occlusal plane optimized for the patient, since some or most of the remaining teeth will not deviate from the occlusal plane in most cases unless all the teeth of the patient has been lost, they may be output while being included in the optimized occlusal plane.

Figure 15:
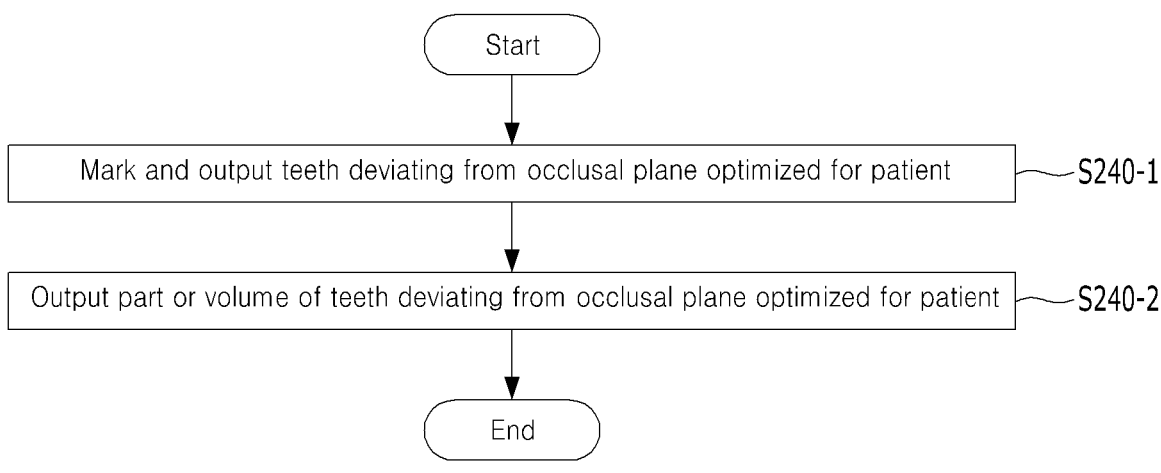
FIG. 15 is a flowchart illustrating specific steps included in step S240.

Furthermore, step S240 may include a step of marking and outputting teeth deviating from the occlusal plane optimized for the patient (S240-1) as shown in FIG. 15.

This is to easily display the teeth deviating from the occlusal plane, and may provide significant convenience to the operator making a plan for dental treatment for the patient on the basis of the occlusal plane optimized for the patient suggested by the occlusal plane suggestion device 100.

Furthermore, referring to FIG. 15, step S240 may include a step of outputting a part or a volume of teeth deviating from the occlusal plane optimized for the patient (S240-2).

Figure 16:
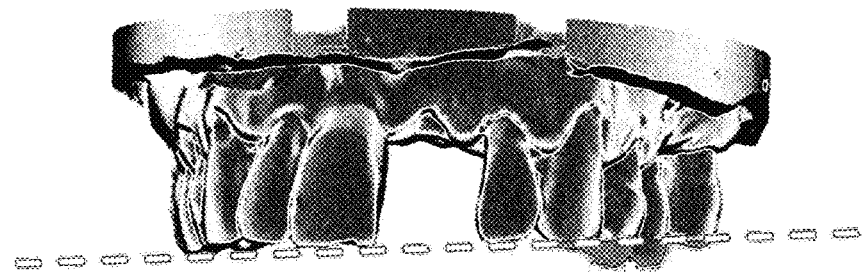
FIG. 16 is a view exemplarily showing an occlusal plane optimized for a patient suggested by an occlusal plane suggestion device and a view of outputting a part of teeth deviating from the occlusal plane.

FIG. 16 is a view exemplarily showing an occlusal plane (dotted line) optimized for a patient suggested by the occlusal plane suggestion device 100 and a view of outputting a part of teeth (the part under the dotted line) deviating from the occlusal plane, and through this, it can be used to make a treatment plan for a patient, and a treatment method for the teeth deviating from the occlusal plane may also be suggested in combination with space analysis of antagonist teeth.

In addition, through this, in the case of the anterior teeth, evaluation of midline deviation and inclination of the occlusal plane (canting) may be confirmed on the basis of the line connecting the patient's pupils, the line connecting the center of the nose in the vertical direction, or the like through matching of facial scan data.

Furthermore, since the first to fourth data and the I-th to IV-th image data are all three-dimensional data, the operator may observe from various angles by rotating the first data of the patient, more specifically, the patient's teeth deviating from the occlusal plane, through an input means such as a keyboard (not shown), a mouse (not shown), or the like, and this is exemplarily shown in FIG. 17.

Meanwhile, the volume of the teeth deviating from the occlusal plane may be output as a number by calculating the volume of the deviating part compared with the volume of corresponding teeth, and whether to output the part or the volume may a choice that can be selected according to setting of the operator.

The part or volume of the patient's teeth deviating from the occlusal plane optimized for the patient described above may be output in correspondence to a threshold value selected by the operator, since suggestion about whether the occlusal plane is appropriate may vary according to the operator. In this case, when the threshold value is set small, the occlusal plane is applied strictly, and the part or volume of teeth deviating from the occlusal plane will also be output strictly, and when the threshold value is set large, the occlusal plane is applied flexibly, and the part or volume of teeth deviating from the occlusal plane will also be output flexibly.

Through adjustment of the threshold value, the operator may separately proceed a treatment plan for improving asymmetry of the dentition and all the teeth deviating from the occlusal plane to be positioned on the optimized occlusal plane, a treatment plan for maintaining current occlusion of the patient, and a camouflage treatment plan for improving a discrepant part of the occlusal plane by finely grinding teeth.

Until now, the occlusal plane suggestion method according to a second embodiment of the present invention has been described. According to the present invention, since an occlusal plane optimized for the patient is suggested only by inputting any one or more among the first to fourth data of the patient into the occlusal plane suggestion device 100, an occlusal plane optimized for the patient may be suggested to have a consistent quality regardless of the clinician's, i.e., operator's, level of skill. In addition, since equipment that is expensive and difficult to maintain such as a face-bow or the like is not required, and it is sufficient to pay only an initial purchase cost for the occlusal plane suggestion device 100 or a predetermined fee for using the device when it is implemented as a server, the patient's burden for the suggestion of an occlusal plane and costs of treatment accompanied thereto can be reduced. In addition, since an operator may separately prepare and proceed various treatment plans by adjusting a threshold value when an occlusal plane optimized for a patient is suggested, a degree of freedom may be guaranteed in establishing a treatment plan.

As the process has been performed up to step S240, the teeth deviating from the suggested occlusal plane may be ground when the deviated part is small, or a crown treatment or a pre-prosthetic orthodontic treatment may be performed thereon, and the size of the teeth dimension on the CBCT data, which is a third data, may be considered in determining a treatment option. Meanwhile, treatment options such as a bridge, an implant, and a denture may be suggested for the parts of lost teeth.

Although it has not been described in detail to avoid redundancy, the occlusal plane suggestion device 100 according to a first embodiment of the present invention and the occlusal plane suggestion method according to a second embodiment of the present invention may be implemented as a computer program stored in a medium according to a third embodiment of the present invention including the same technical features. In this case, the computer program stored in a medium may execute, in combination with a computing device, the steps of (AA) receiving any one or more among first to fourth data of a normal occlusion person, and generating an IV-th image data by matching the data, (BB) analyzing the generated IV-th image data, and learning the relation between landmarks, which are anatomical singularities, and the occlusal plane of a normal occlusion person; (CC) receiving any one or more among first to fourth data of a patient; and (DD) analyzing the first data of the patient on the basis of the learned relation between the landmarks and the occlusal plane of a normal occlusion person, and outputting a suggestion of an occlusion plane optimized for the patient.

Although the embodiments of the present invention have been described with reference to the accompanying drawings, those skilled in the art may understand that the present invention may be embodied in other specific forms without changing its technical spirit or essential features. Therefore, the embodiments described above should be understood as illustrative and not limiting in all respects.

The invention claimed is:

1. An occlusal plane suggestion method comprising the steps of:
   (a) receiving, by an occlusal plane suggestion device, any one or more among first to fourth data of a normal occlusion person, and generating an IV-th image data by matching the received data, wherein any one among the first to fourth data comprise three-dimensional image data including any one among oral cavity scan data or oral model scan data, face scan data with teeth exposed, computed tomography (CT) data, cone beam computed tomography (CBCT) data, and face scan data without teeth exposed;
   (b) analyzing the generated IV-th image data, and learning, by the occlusal plane suggestion device, a relation between landmarks, which are anatomical singularities, and an occlusal plane of the normal occlusion person, wherein any one or more among the CBCT data and the face scan data without teeth exposed are data marked with the landmarks;
   (c) receiving, by the occlusal plane suggestion device, any one or more among first to fourth data of a patient, wherein any one among the first to fourth data of the patient comprise three-dimensional image data including any one among oral cavity scan data or oral model scan data, face scan data with teeth exposed, CT data, CBCT data, and face scan data without teeth exposed; and
   (d) analyzing any one or more among the received first to fourth data of the patient on the basis of the learned relation between the landmarks and the occlusal plane of the normal occlusion person, and outputting a suggestion of an occlusion plane optimized for the patient, by the occlusal plane suggestion device.

2. The method according to claim 1, wherein the step (a) includes the steps of:
   (a-1) generating I-th image data by matching oral cavity scan data or oral model scan data, which is a first data of a normal occlusion person, and face scan data with teeth exposed, which is a second data;

(a-2) generating II-th image data by matching oral cavity scan data or oral model scan data, which is a first data of a normal occlusion person, and CBCT data, which is a third data;
   (a-3) generating III-th image data by matching face scan data with teeth exposed, which is a second data of a normal occlusion person, and face scan data without teeth exposed, which is a fourth data; and
   (a-4) generating IV-th image data by matching the I-th image data, the II-th image data, and the III-th image data.

3. The method according to claim 2, further comprising, after the step (a-4), the step of (a-5) removing the face scan data with teeth exposed, which is a second data, from the IV-th image data.

4. The method according to claim 2, wherein the I-th image data is generated by matching the oral cavity scan data or oral model scan data, which is a first data of a normal occlusion person, and the face scan data with teeth exposed, which is a second data, on the basis of teeth of an anterior exposed area.

5. The method according to claim 2, wherein the II-th image data is generated by matching the oral cavity scan data or oral model scan data, which is a first data, and the CBCT data, which is a third data, on the basis of entire teeth.

6. The method according to claim 1, wherein the first data of the patient comprises oral cavity scan data or oral model scan data of the patient.

7. The method according to claim 1, wherein the landmarks are any one or more among nasion, glabella, exocanthion right, exocanthion left, endocanthion right, endocanthion left, pronasale, subnasale, alar right, alar left, crista philtri right, crista philtri left, labiale superious, chellion right, chellion left, stomion, labiale inferious, sublabiale, pogonion, gnathion, menton, tragus right, tragus left, gonion right, gonion left, tragion, basion, anterior nasal spine, posterior nasal spine, point a (point of maximum midline concavity on the maxilla), point b (point of maximum midline concavity on the mandibular symphysis), pogonion, menton, gnathion, left porion, right porion, left orbitale, right orbitale, left condylion, right condylion, left gonion, right gonion, left zygion, and right zygion.

8. The method according to claim 1, wherein the learning at the step (b) is a learning using any one or more among a generative adversarial network (GAN) and a volume-to-volume regression.

9. The method according to claim 1, wherein the step (d) includes the steps of:
   (d-1) marking and outputting teeth of the patient deviating from the suggested occlusal plane optimized for the patient; and
   (d-2) outputting a part or a volume of the teeth of the patient deviating from the suggested occlusal plane optimized for the patient.

10. The method according to claim 9, wherein the part or volume of the teeth of the patient deviating from the suggested occlusal plane optimized for the patient is output in response to a selected threshold value.

11. An occlusal plane suggestion device comprising:
   one or more processors;
   a network interface;
   a memory for loading a computer program executed by the processor; and
   a storage for storing large-capacity network data and the computer program, wherein
   the computer program executes, by the one or more processors, (A) an operation of receiving any one or more among first to fourth data of a normal occlusion person, and generating an IV-th image data by matching the received data, wherein any one among the first to fourth data comprise three-dimensional image data including any one among oral cavity scan data or oral model scan data, face scan data with teeth exposed, computed tomography (CT) data, cone beam computed tomography (CBCT) data, and face scan data without teeth exposed;

(B) an operation of analyzing the generated IV-th image data, and learning a relation between landmarks, which are anatomical singularities, and an occlusal plane of the normal occlusion person, wherein any one or more among the CBCT data and the face scan data without teeth exposed are data marked with the landmarks;

(C) an operation of receiving any one or more among first to fourth data of a patient, wherein any one among the first to fourth data of the patient comprise three-dimensional image data including any one among oral cavity scan data or oral model scan data, face scan data with teeth exposed, CT data, CBCT data, and face scan data without teeth exposed; and (D) an operation of analyzing any one or more among the received first to fourth data of the patient on the basis of the learned relation between the landmarks and the occlusal plane of the normal occlusion person, and outputting a suggestion of an occlusion plane optimized for the patient.

12. A non-transitory computer-readable medium to execute, in combination with a computing device, the steps of:

(AA) receiving any one or more among first to fourth data of a normal occlusion person, and generating an IV-th image data by matching the received data, wherein any one among the first to fourth data comprise three-dimensional image data including any one among oral cavity scan data or oral model scan data, face scan data with teeth exposed, computed tomography (CT) data, cone beam computed tomography (CBCT) data, and face scan data without teeth exposed;

(BB) analyzing the generated IV-th image data, and learning a relation between landmarks, which are anatomical singularities, and an occlusal plane of the normal occlusion person, wherein any one or more among the CBCT data and the face scan data without teeth exposed are data marked with the landmarks;

(CC) receiving any one or more among first to fourth data of a patient, wherein any one among the first to fourth data of the patient comprise three-dimensional image data including any one among oral cavity scan data or oral model scan data, face scan data with teeth exposed, CT data, CBCT data, and face scan data without teeth exposed; and (DD) analyzing any one or more among the received first to fourth data of the patient on the basis of the learned relation between the landmarks and the occlusal plane of the normal occlusion person, and outputting a suggestion of an occlusion plane optimized for the patient.

* * * * *